United States Patent [19]

Konstantinova et al.

[11] Patent Number: 5,095,108

[45] Date of Patent: Mar. 10, 1992

[54] NON-SOLVATED CRYSTALLINE FORM "A" OF 3-(4-CYNNAMYL-1-PIPERAZINYL-)IMINOMETHYLRIFAMYCINE SV AND A METHOD OF ITS PRODUCTION

[75] Inventors: Rumyana G. Konstantinova; Anka V. Evstatieva; Ivan A. Again; Velichka Dimova, all of Sofia, Bulgaria

[73] Assignee: Technologichen Kombinat za Promishlena Microbiologia, Razgraol, Bulgaria

[21] Appl. No.: 575,387

[22] Filed: Aug. 28, 1990

[51] Int. Cl.$^5$ .................. C07D 498/22; A61K 31/495
[52] U.S. Cl. ..................................... 540/458; 540/457
[58] Field of Search ............................. 540/458, 457

[56] References Cited

U.S. PATENT DOCUMENTS

| | | | |
|---|---|---|---|
| 4,193,920 | 3/1980 | Konstantinova et al. | 540/458 |
| 4,774,237 | 9/1988 | Ueno et al. | 540/458 |
| 4,876,258 | 10/1989 | Kump et al. | 540/458 |

OTHER PUBLICATIONS

Konstantinova et al., CA 93-72212p, (1980).

Dimova et al., CA 106-12417m, (1987).

*Primary Examiner*—Cecilia Shen

[57] ABSTRACT

The non-solvated crystalline form "A" of 3-(-4-cynnamyl-1-piperazinyl)-iminomethylrifamycine SV finds application in the therapeutical practice.

It represents a crystalline substance with absorption maximum of the infrared spectrum at 1644, 1585, 1340, 1350, 1295 and 1290-doublet, 1238, 1213, and triplet with low intesitivety at 726, 735 and 760 cm$^{-1}$, as well as with characteristic diffraction maxima at 9,25 and 9,50 $\theta$—most-intensive at 12,22 and doublet at 13,10 and 13,33 $\theta$ of the X-ray diffraction diagram.

The obtaining of the non-solvated crystalline form "A" consists in the isolation of 3-(-4-cynnamyl-1-piperazinyl)-iminomethylrifamycine obtained in medium of indifferent organic solvent, preferably tetrahydrofuran or chloroform, and its dissolution in isopropanol or acetone or a mixture of both at a temperature from 30° C. up to the ebullition temperature of the respective solvent.

The substance possesses a high resoptionability, a high serum concentration, stability and chemical resistance.

1 Claim, 8 Drawing Sheets

FIG. 1

FIG. 2

INFRARED SPECTRUM OF CRYSTAL FORM CI / SOLVATE WITH CHCL$_3$ /

NON-SOLVATED CRYSTALLINE FORM "A" OF 3-(4-CYNNAMYL-1-PIPERAZINYL)IMINOMETHYLRIFAMYCINE SV AND A METHOD OF ITS PRODUCTION

The present invention relates to the non-solvated crystalline form "A" of 3-(-4-cynnamyl-1-piperazinyl)-iminomethylrifamycine SV which is biologicaly active and to a method of its production. The compound belongs to the group of the semi-synthetic ansamycines and possesses a high activity against gram-positive (aerobic, anaerobic and tuberculous) and gram-negative microorganisms in vitro and in vivo. In the case of experimental generalized tuberculosis of guinea-pigs the compound manifests a the rapeutic effect with a eight times lower dose in comparison with the dose of the rifamycine.

A derivative of the rifamycine SV (formula I) is known (1):

Its therapeutic effect is manifested at a dose eight times lower in comparison with the dose of the tubocine whereupon the LD$_{50}$ for white mice is 40000 mg/k of weight and for the tubocine—1500 mg/k of weight. All this determines the compound as the most advanced one from the group of the rifamycine derivatives quoted in (1).

From the literature it is known that the tubocine itself exists in different polymorphic forms whereas according to the mode of obtaining or of purification could be obtained different non-solvated crystalline forms and also solvates with different solvents (2).

The task of the present invention is the creation of a new non-solvated crystalline form of the compound which must be stable at stockage and with an improved solvability and resorption in the organism.

This task is solved by the non-solvated crystalline form "A" 3-(-4-cynnamyl-1-piperazinyl)-iminomethyl-rifamycine SV with the following formula:

and an infrared spectrum recorded in a newoil suspension with absorption maxima at 1644, 1585, 1340, 1350, 1295 and 1290—doublet, 1238, 1213 and triplet with a low intensity at 726, 735 and 760 cm$^{-1}$ as well as with diffraction maxima at 9,25 and 9,50$\theta$—most intensive at 12,22 and doublet at 13,10 and 13,33$\theta$ in the X-ray diffraction diagram.

The method for the obtaining of the non-solvated crystalline form "A" consists in the following: the 3-(4-cynnamyl-1-piperazinyl)-iminomethylrifamycine SV obtained in a medium of indifferent organic solvent, preferably the tetrahydrofuran or the chloroform, is isolated and dissolved into isopropanol or acetone, or a mixture of both at a temperature from 30° C. up to the temperature of ebullition of the respective solvent.

The ration of the substance (in grams) to the solvent (in ml) depends of the solvability of the compound in the respective solvent. With the isopropanol this ratio is 1 g to 70 ml; with the acetone—1 g to 15 ml.

According to the invention it is preferable to utilize a mixture of both solvents(isopropanol and acetone) in a ratio of 1:1 as solvent for the obtaining the crystalline form "A".

When dissolving the crystalline form "A" in chloroform and after a fast evaporation of the solvent, it is obtained the crystalline form marked as "CI".

At the crystallyzation of the crystalline form "A" in the tetrachloromethan or in the methanol are obtained the respective solvated forms "CII" and "CIII".

The advantages of the present invention are as follows: the crystalline form "A" possesses a fast resorption, a high serum concentration, a good chemical stability, a resistance at normal conditions of stockage; the compound is easy obtained in a crystallographic pure state.

The following examples illustrate more in detail the invention.

EXAMPLE 1

A. Obtaining of 3-(4-cinnamyl-1-piperazinyl)-iminomethyl rifamycine SV.

3,6 g (0,005 mol) 3-formyl rifamycine SV is dissolved into 30 ml of chloroform and to the solution are added at continuous stirring 1,2 g (0,0055 mol) N$^1$-cinnamyl-N$^4$-amino piperazine, dissolved in 10 ml of chloroform. The reacting mixture is stirred at room temperature for 1 hour and afterward the solvent is distilled under reduced pressure to its entire elimination. To the residue are added 30 ml of diisopropylether and is deposited for one night in the refrigerator. The dark-red precipitation is filtered, rinsed with diisopropylether and dryed at 60° C. The yield is 4,13 g as technical product.

B. Recrystallysation of the technical product under the conditions to obtain the non-solvated form "A".

To 4,15 g of the technical product, obtained according to the aforementioned method are added 290 ml of isopropanol. The reactive mixture is heated to ebullition and the solution is filtered hot and the filtrate is cooled at stirring to 10° C. The deposited crystals are filtered and rinsed with cooled isopropanal. After drying are obtained 3,7 g non-solvated crystalline form "A" of 3-(-4-cynnamyl-1-piperazinyl)-iminomethyl rifamycine SV possessing the following characteristics:

Infrared spectra with the following intensive bands: 1644, 1585, 1340, 1350, 1295 and 1290;

Diffraction maxima at: 9,25 and 9,50θ.

EXAMPLE 2

3 g of the obtained according to the example 1A technical product are recrystallised at conditions analogous of these discribed in Example 1B, whereas instead of 290 ml isopropanol are used 45 ml acetone. 2,1 g of a crystal substance are obtained corresponding to the infrared spectrum of the form "A".

After dissolving the crystal form A in chloroform and after a fast evaporation of the solvent, is obtained the solvated crystalline form marked as "CI".

The crystallisation of the crystalline form "A" with tetrachloromethan or methanol leads to the respective solvated forms "CII" and "CIII".

The different crystalline forms are identified by the infrared spectra of the suspensions in newoil, by the X-ray diffraction of the powder samples and the thermic analysis.

Figure 1:
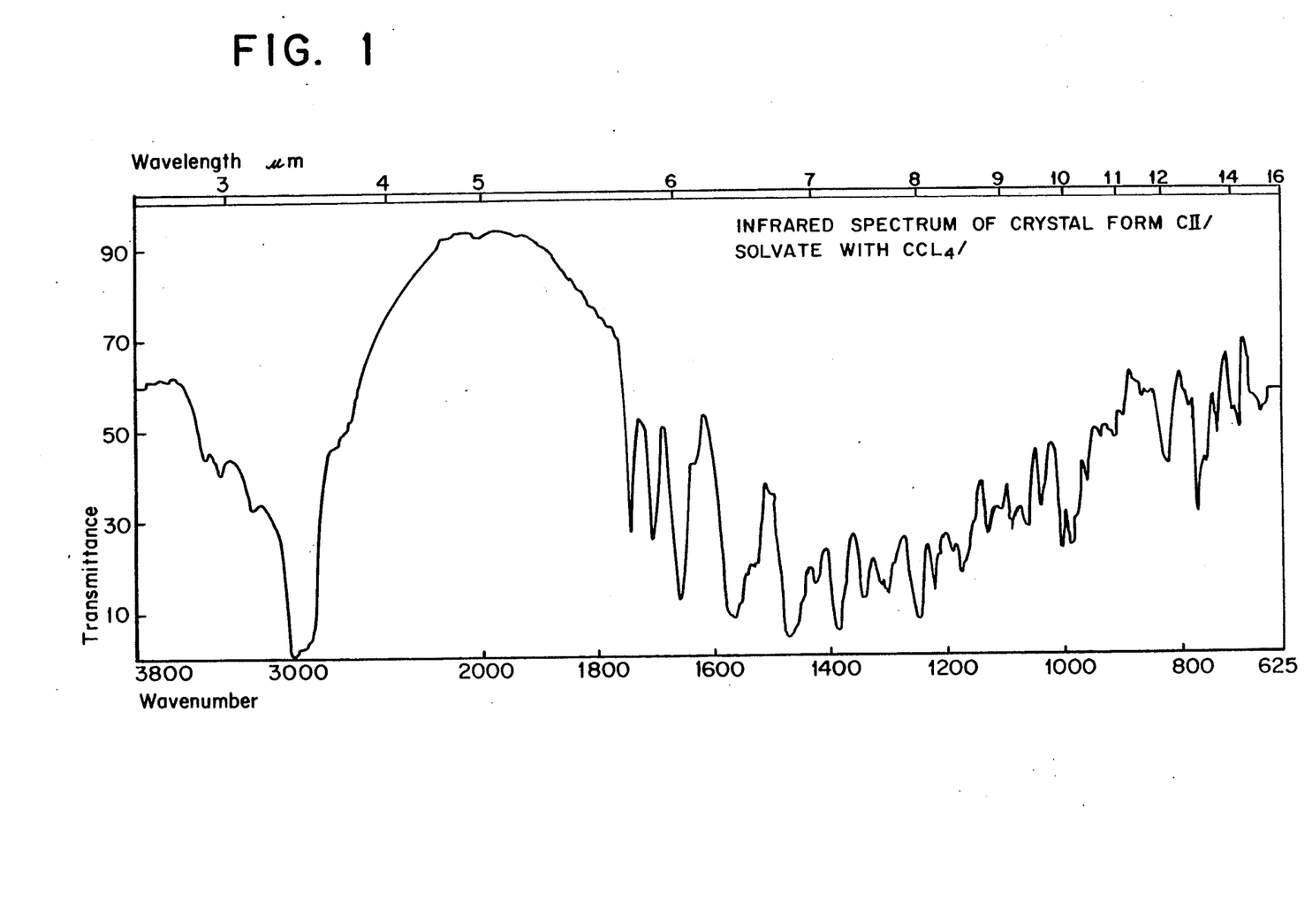
Figure 2:
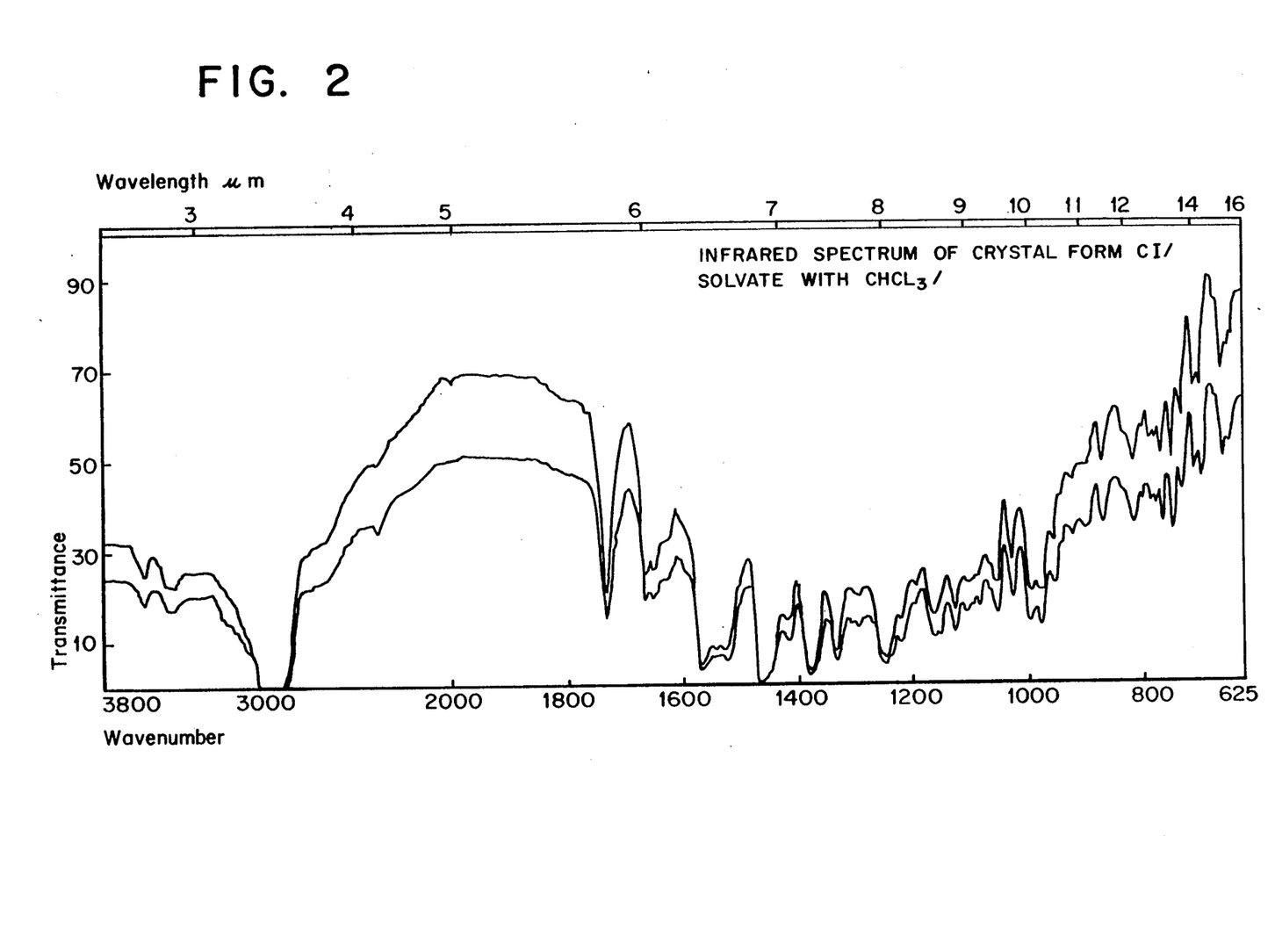
Figure 3:
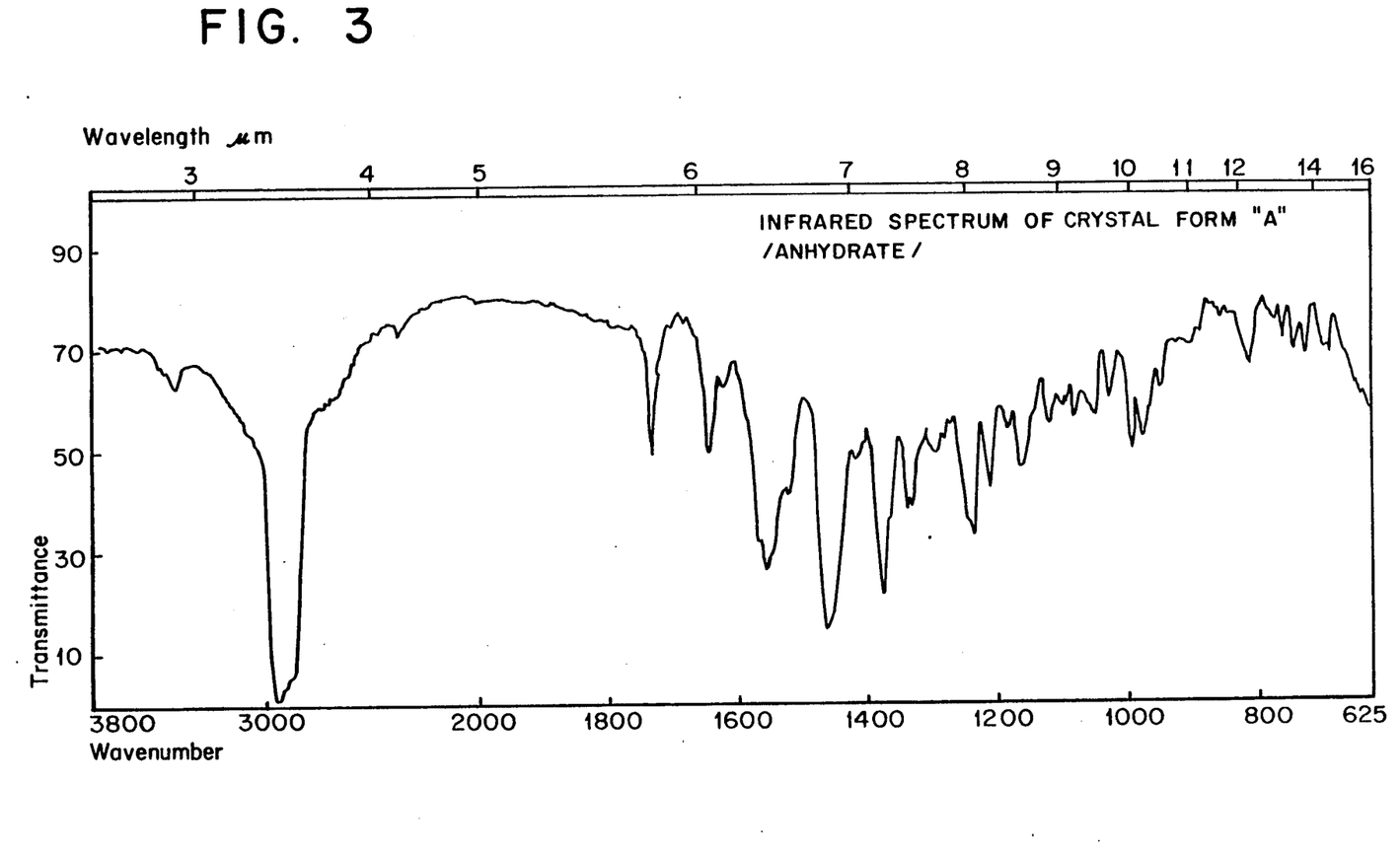
Figure 4:
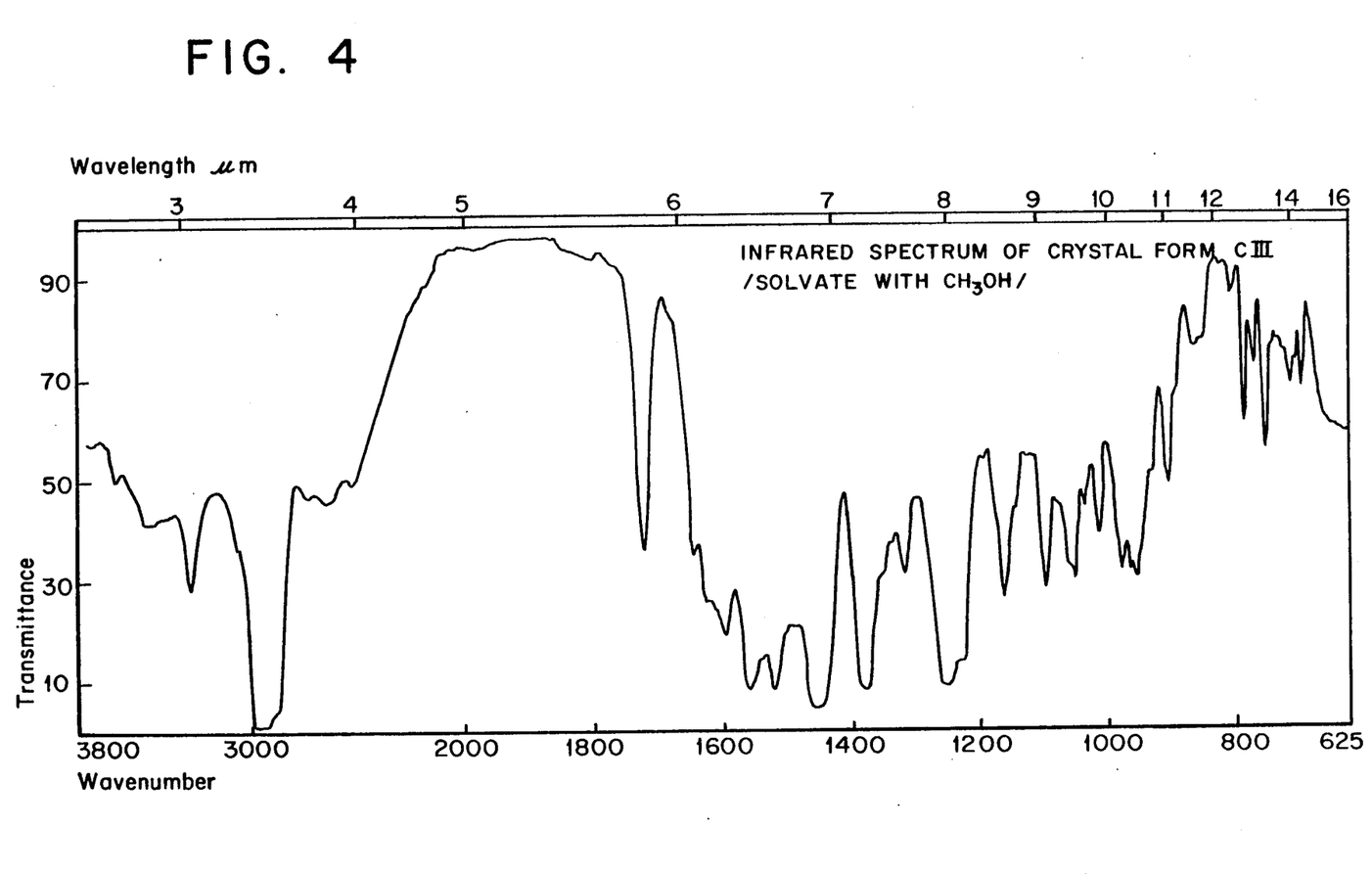

On the FIGS. 1, 2, 3 and 4 are shown the infrared spectra of the different crystalline forms, which differ substantialy in respect to the position and the intensities of the absorption bands, especially in the region from 2000 up to 1300 $cm^{-1}$. The characteristic absorption bands in the infrared spectra which can be used for the identification of the different forms are shown on the table 1.

The infrared spectra of the four crystalline forms are obtained by means of the standard method of newoil suspension, which method appears to be fast and convinient. The spectra are recorded on a Pye Unicame apparatus—model 1000.

Figure 5:
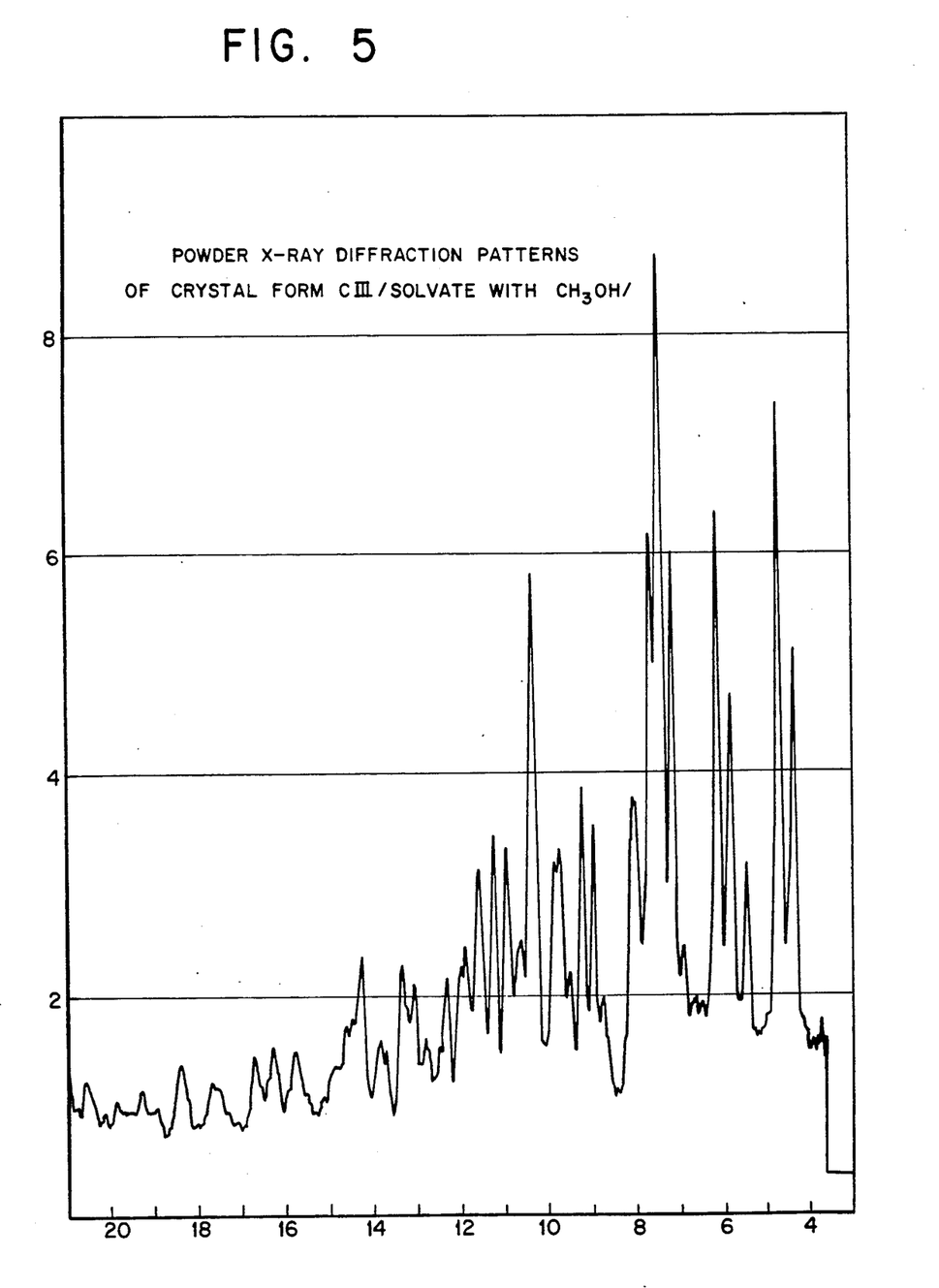
Figure 6:
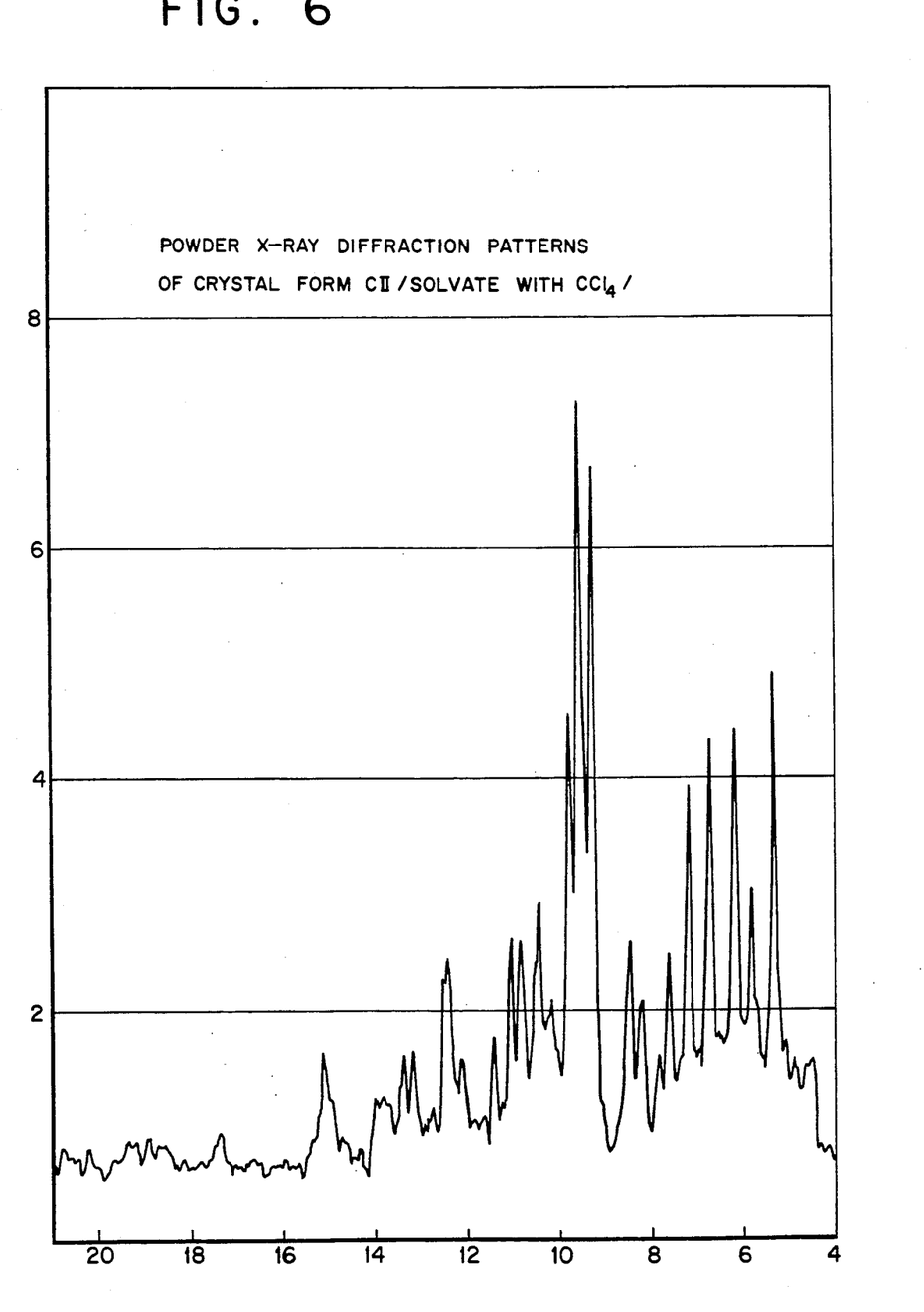
Figure 7:
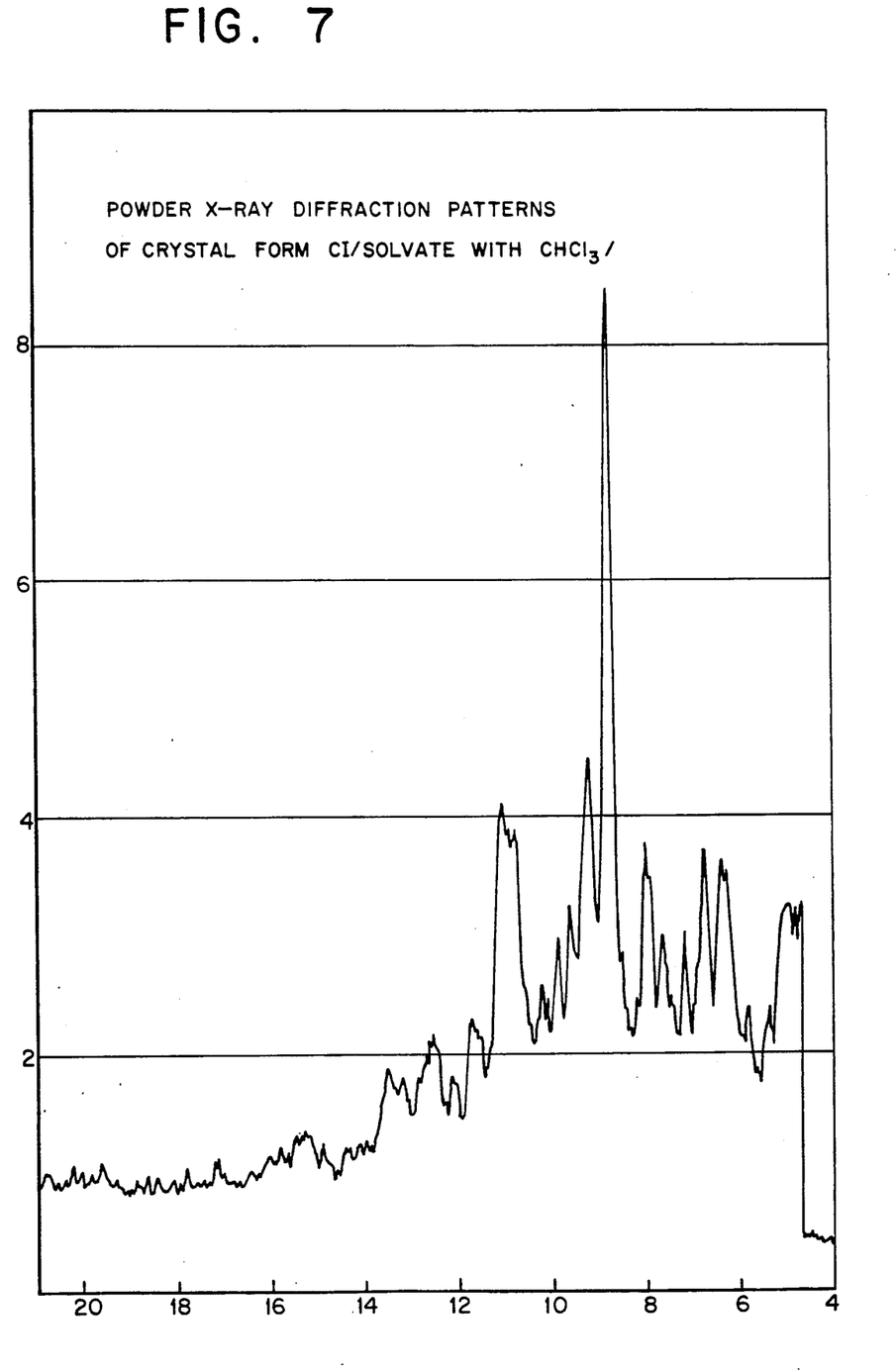
Figure 8:
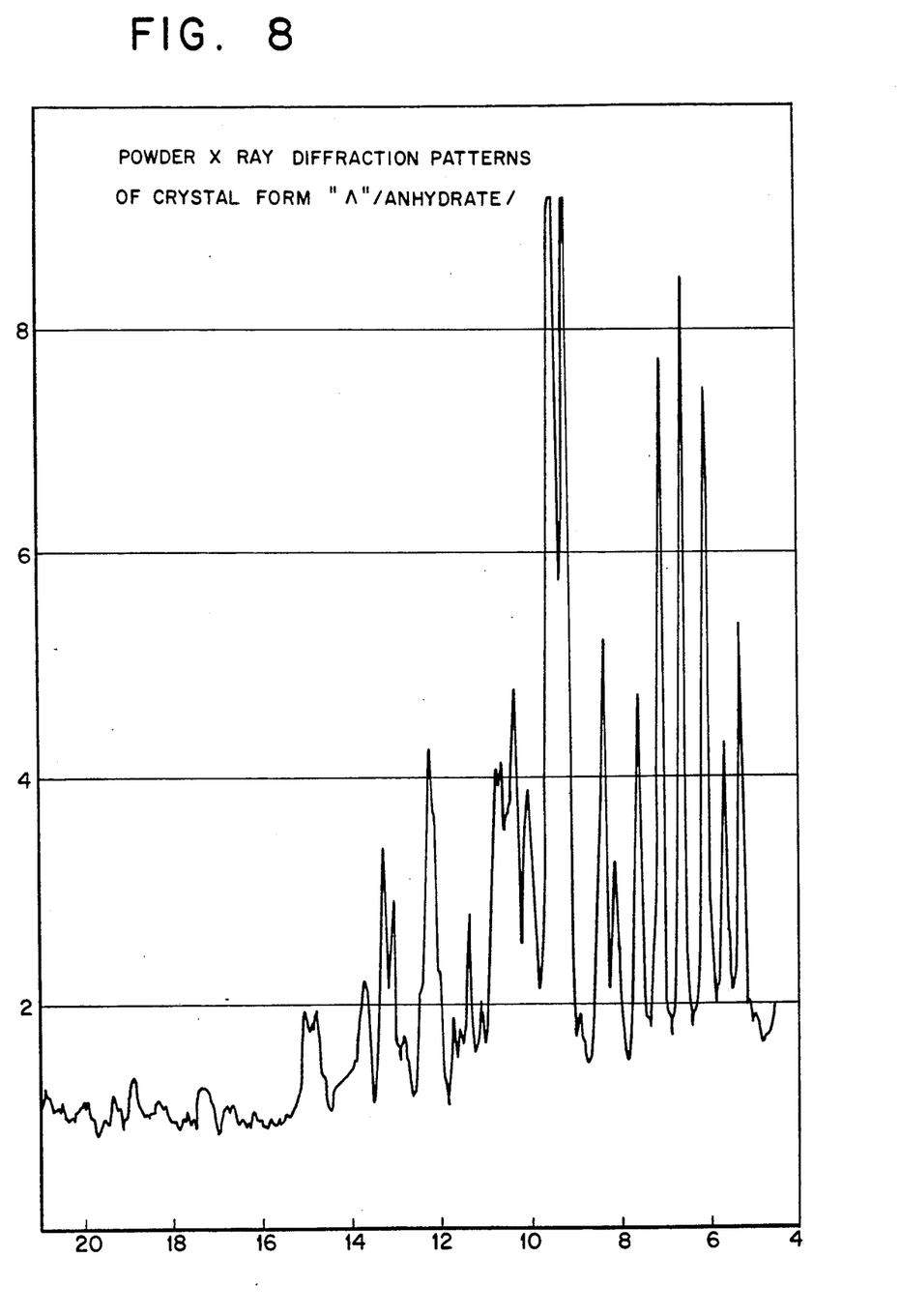

From the X-ray diagrams (FIGS. 5,6,7 and 8) it appears that the diffraction maxima are in the region from 5 up to 20θ (θ=diffraction angle) for all the forms, but they differ substantially in respect to the position and the relative intensity which is an evidence of the presence of the four different crystalline forms (structures). On the table 2 are given the peak values of the diffraction angle θ which can be used to distinguish one form from another.

The solvated forms are identified by means of the thermogravimetric method by the loss of the weight.

Pharmacokinetic investigations are carried out with the four crystalline forms upon control animals—white mice, in order to determine their serum concentration. The control animals are feed per os with a 10% aqueous solution of Twin 80 suspensions of the four crystalline forms with doses of 40 mg/k of weight. The blood assays are taken 15, 30 and 60 minutes after the intake. The serum concetration of the different crystalline forms are determined at the intervals after centrifugation according to the diffusion method in agar medium of Rendel by means of the strain Micrococus Luteus ATCC 9341 in respect to the tubocine standard. The results are shown on the table 3.

From the table it appears that the crystalline form "A" has the fastest resorption and achieves a serum concentration comparable with the concentrations of the tubocine.

It is worth to be noted that the form "A" possesses a therapeutical effect of eight times lower dose in comparison to the dose of the tubocine.

The investigations for the stability of the form "A" are carried out at loose state of a sample held at 50° C. and a sample exposed at the sunlight at 25° C. After a period of 6 and 12 weeks the samples are examined for visual or chemical modifications. It is established that the samples possess a good chemical stability. The investigations upon the different crystalline forms of the compound of the form "A" show:

1. The fastest resorption and the higher serum concentrations.
2. Stability at normal conditions of shelf life.
3. Readily obtaining in the crystallographic pure state.

TABLE 1

| CHARACTERISTIC ABSORPTION BANDS IN THE INFRARED SPECTRA OF THE DIFFERENT CRYSTALLINE FORMS (in $cm^{-1}$) | | | | | | |
|---|---|---|---|---|---|---|
| Nonsolvated form "A" | Solvate with $CHCl_3$ C I | | Solvate with $CCl_4$ C II | | Solvate with $CH_3OH$ C III | |
| 3420 | 3580 | | 3360 | | 3620 | |
| 1644 | 3450 | | 3200 | | 3280 | |
| 1555 | | | 1703 | | 1720 | |
| 1460 | 1665 | wide triplet | 1385 | | | |
| | 1650 | | 1300 | | 1645 | wide triplet |
| 1340 } doublet | 1625 | | 1180 | | 1630 | |
| 1350 | | | 1090 | | 1600 | |
| | 1420 | | 1030 | | | |
| 1295 } doublet | 1335 | | | | 1450 | |
| 1290 | | | 940 } triplet | | 1315 | |
| | 1000 } triplet | | 915 | | 1100 | |
| 1238 | 980 | | 900 | | 1065 | |
| 1213 | 953 | | | | 1050 | |
| | | | 770 | | 1015 | |
| 760 | 920 | | 755 | | | |

TABLE 1-continued

CHARACTERISTIC ABSORPTION BANDS IN THE INFRARED SPECTRA OF THE DIFFERENT CRYSTALLINE FORMS (in $cm^{-1}$)

| Nonsolvated form "A" | | Solvate with $CHCl_3$ C I | | Solvate with $CCl_4$ C II | | Solvate with $CH_3OH$ C III | |
|---|---|---|---|---|---|---|---|
| 735 | triplet | | doublet | 715 | | 980 | |
| 726 | | 895 | | 700 | | 955 | triplet |
| | | 775 | | | | 905 | |
| 700 | | 748 | triplet | | | | |
| 690 | doublet | 730 | | | | 785 | |
| | | 710 | | | | 760 | triplet |
| | | | doublet | | | 753 | |
| | | 700 | | | | 715 | |
| | | | | | | | doublet |
| | | | | | | 697 | |

TABLE 2

CHARACTERISTIC DIFFRACTION PEAKS IN THE X-RAY DIAGRAMS OF THE DIFFERENT CRYSTALLINE FORMS (in diffraction angles $\theta$)

| Non-solvated form "A" | | Solvate with $CHCl_3$ C II | | Solvate with $CCl_4$ C III | | Solvate with $CH_3OH$ C IV | |
|---|---|---|---|---|---|---|---|
| 5,4 | | 6,3 | | 5,3 | | 5,5 | |
| 5,6 | | 6,8 | | | | | |
| 6,1 | | 8,8 | most intensive | 9,3 | intensive triplet | 7,2 | most intensive triplet |
| | | | | 9,6 | | 7,5 | |
| 9,2 | most intensive doublet | | | 9,8 | | 7,7 | |
| 9,5 | | 10,8 | | | | 8,0 | |
| | | 11,1 | | 10,5 | triplet | 8,1 | |
| 10,1 | | | | 10,8 | | | |
| | | | | 11,0 | | | |
| 10,6 | doublet | | | | | 9,0 | |
| 10,7 | | | | 11,4 | | 10,4 | |
| | | | | 12,4 | | | |
| 12,2 | | | | | | 11,0 | |
| | | | | | | 11,3 | triplet |
| 13,1 | doublet | | | | | 11,6 | |
| 13,3 | | | | | | | |
| | | | | | | 13,1 | doublet |
| | | | | | | 13,4 | |
| 14,8 | doublet | | | | | 14,3 | |
| 15,1 | | | | | | | |

TABLE 3

SERUM CONCENTRATIONS OF THE DIFFERENT CRYSTALLINE FORMS IN CONTROL ANIMALS AFTER PER OS INTAKE OF A DOSE 40 mg/k of weight (microgram/ml)

| Form | Minutes after the intake | | |
|---|---|---|---|
| | 15 | 30 | 60 |
| C I | 6,2 | 8,6 | 8,8 |
| C II | 2,4 | 4,2 | 3,6 |
| C III | 4,0 | 6,8 | 7,6 |
| C IV | 1,8 | 3,6 | 3,2 |
| Tubocine | 6,8 | 8,8 | 10,10 |

We claim:

1. Non-solvated crystalline form "A" of 3-(-4-cynnamyl-1-piperazinyl)-iminomethyl rifamycine SV of formula:

and with infrared spectrum recorded in newoil suspension, with absorption maxima at 1644, 1585, 1340, 1350, 1295 and 1290-doublet, 1238, 1213 and triplet with low intensity at 726, 735 and 760 $cm^{-1}$ and with characteristic diffraction maxima at 9,25 and 9,50$\theta$—most intensive, at 12,22 and doublet at 13,10 and 13,33$\theta$ of the X-ray diffraction diagram.

* * * * *